United States Patent [19]
Sweet

[11] Patent Number: 4,630,468
[45] Date of Patent: Dec. 23, 1986

[54] VISCOMETER

[75] Inventor: Edmund G. F. Sweet, Ontario, Canada

[73] Assignee: Ontario Research Foundation, Mississauga, Canada

[21] Appl. No.: 536,307

[22] Filed: Sep. 27, 1983

[30] Foreign Application Priority Data

Aug. 9, 1983 [CA] Canada .................................. 434176

[51] Int. Cl.⁴ .......................................... G01N 11/14
[52] U.S. Cl. ...................................................... 73/59
[58] Field of Search ................................ 73/59, 60, 54

[56] References Cited

U.S. PATENT DOCUMENTS

| | | | |
|---|---|---|---|
| 1,836,995 | 12/1931 | Stickney | 73/59 |
| 1,982,328 | 11/1934 | Stickney | 73/59 |
| 2,096,222 | 10/1937 | Bock | 73/59 |
| 2,643,543 | 6/1953 | Herzog | 73/59 |
| 2,703,006 | 3/1955 | Savins | 73/59 |
| 3,343,405 | 9/1967 | Gilinson, Jr. et al. | 73/59 |
| 3,435,666 | 4/1969 | Fann | 73/59 |
| 3,803,903 | 4/1974 | Lin | 73/59 |
| 3,935,726 | 2/1976 | Heinz | 73/60 |
| 4,062,225 | 12/1977 | Murphy, Jr. et al. | 73/60 |
| 4,175,425 | 11/1979 | Brookfield | 73/59 |

FOREIGN PATENT DOCUMENTS

| | | | |
|---|---|---|---|
| 844362 | 7/1952 | Fed. Rep. of Germany | 73/59 |
| 602824 | 4/1978 | U.S.S.R. | 73/60 |

Primary Examiner—Stewart J. Levy
Assistant Examiner—Hezron E. Williams
Attorney, Agent, or Firm—Sim & McBurney

[57] ABSTRACT

A method and apparatus are provided for measuring the viscosity of a fluid medium such as drilling mud. A rotary member is mounted within a housing for free rotation and viscous drag means applies a torque-induced rotation to the rotary member. The rotary member has a portion moving adjacent to a fixed surface but out of contact with the fixed surface, thus defining a fluid cavity in which the fluid medium to be tested can be placed, in order to be sheared by relative movement between the portion and the fixed surface. Means are provided to measure the rotational speed of the rotary member, whereby the geometry of the fluid cavity and the nature of the viscous drag means can be used in a determination of the viscosity of the fluid medium to be tested.

31 Claims, 5 Drawing Figures

VISCOMETER

This invention relates generally to viscometers, and has to do particularly with a viscometer capable of making rheological measurements on liquids under conditions of high temperature and high pressure. Even more particularly, the viscometer set forth herein is adapted to measure the viscosity of drilling mud under conditions of temperature and pressure approximating those found in the bore-hole under actual drilling conditions.

BACKGROUND OF THIS INVENTION

The prior art contains numerous viscometer constructions. The most common form of viscometer is one in which a first rotary member has an outer surface of revolution which rotates closely adjacent to, but out of contact with, an inner surface of revolution on a second rotary member. The space between the two surfaces defines a cavity in which can be placed a liquid of which the rheological properties are to be determined. Means are typically provided for rotating one of the rotary members, while the other rotary member is placed under a resilient restraint which is such that the extent of displacement of the restrained rotary member from its "at rest" position corresponds linearly with the amount of torque to which it is subjected. The measurement of the displacement, taken together with the geometric properties of the cavity in which the liquid is placed and the rotational speed of the rotating member, permits a calculation of the viscosity of the liquid.

Exemplary of this prior art construction is U.S. Pat. Nos. 4,062,225, Murphy et al, issued Dec. 13, 1977, and 4,045,999, Palmer, issued Sept. 6, 1977.

Almost all of these prior art constructions, as exemplified by the patents just listed, require the liquid to be tested at atmospheric pressure. No capability is present to test the liquid at elevated pressure, or at elevated temperatures.

Another approach taken in the prior art is exemplified by U.S. Pat. No. 3,667,286, Kaufman et al, in which a rotating element has a portion floating in an angular trough, and has a central hub floating in a cylindrical trough. A Newtonian fluid is placed in one of the troughs, and the other trough is filled with the liquid to be tested. The means defining one of the troughs is rotated in a first direction, while the means defining the other of the troughs is rotated in the opposite direction, and these rotational speeds are adjusted until the rotary floating member comes to a standstill. Then, the geometry of the troughs and the relative speeds of rotation can be utilized to calculate the rheological properties of the test liquid. This patent also requires testing to take place at atmospheric pressure, and has no capability of testing at elevated pressures or elevated temperatures.

As is well known, drilling mud is utilized in well-drilling operations for a number of basic purposes. One purpose is to cool and lubricate the bit and the string. Another is to carry up to the surface the chips of rock, etc. which are produced as a result of the drilling operation. A third purpose is to "cake" against the sides of the bore-hole and thus block up the tiny interstices in the rock wall through which the aqueous portion of the drilling mud could escape. A fourth is to control the pressure in the well in order to prevent blow out due to a higher pressure in the formation than in the well. A fifth is for control of corrosion of the string and bit. A sixth purpose is to stabilize the well bore chemistry. A seventh is to buoyantly support the drill string.

Due to geophysical heat in the surrounding formation, the temperature of the drilling mud can rise as high as 600° F. or more. The pressure of the drilling mud depends, of course, upon the depth of the bore-hole. For very deep wells, the pressure placed upon the drilling mud at the bottom of the well can be as high as 20,000 psi or more.

The viscosity of a drilling mud is one of the characteristics which determines how efficiently the drilling mud will carry rock chips, etc. up to the surface. Another factor is the Specific Gravity of the drilling mud.

It is very desirable to be able to measure the viscosity of the drilling mud under conditions which approximate those found under operating conditions, namely at elevated temperatures and pressures. Accordingly, it is an object of an aspect of this invention to provide a viscometer structure which can be pressurized to high pressures and yet function reliably. It is an object of a further aspect of this invention to provide a viscometer structure in which at least the portion in contact with the drilling mud (or other fluid to be tested) may be raised to an elevated temperature without interfering with the operation of the device.

An object of another aspect of this invention is to provide a viscometer in which the measurement range can be adjusted either very slightly or by a substantial amount.

In accordance with this invention, the basic viscometer structure comprises means for rotating a first member at an accurately known rate, and a freely turning rotary member having an axis of rotation and having a first portion adjacent the first member but out of contact with it. A first fluid cavity is thus defined between the first member and the first portion, and a fluid is located in the first fluid cavity such that rotation of the first member will place torque on the rotary member thus seeking to induce rotation therein. The first fluid is preferably a Newtonian fluid such as oil, of which the rheological properties are known.

The rotary member further has a second portion moving adjacent a fixed surface but out of contact therewith, thus defining a second fluid cavity between the second portion of the fixed surface into which can be placed the fluid medium, for example the drilling mud, of which the viscosity is to be measured. The apparatus further includes means to measure the rotational speed of the rotary member.

Additionally, this invention provides a method of measuring the viscosity of a fluid medium, such as drilling mud, comprising several steps. Viscous drag means are used for applying a torque-induced rotation to a rotary member, in such a way that the torque on the rotary member can be known. The fluid medium to be tested in placed in a fluid cavity defined between a portion of the rotary member and a fixed surface, and the torque applied to the rotary member through the viscous drag thereon is determined from a prior calibration. The viscosity of the fluid medium is then determined from the geometry of the fluid cavity, the known torque on the rotary member, and the rotational speed of the rotary member, the latter being measured as one of the steps.

Some drilling muds are non-Newtonian (thixotropic), and the present apparatus is adapted for measuring the viscosity of either Newtonian or non-Newtonian liquids.

GENERAL DESCRIPTION OF THE DRAWINGS

One embodiment of this invention is illustrated in the accompanying drawings, in which like numerals denote like parts throughout the several views, and in which:

FIG. 2 is a partial axial sectional view, to a larger scale, through the lower portion of the viscometer shown in FIG. 1a;

Figure 1A:
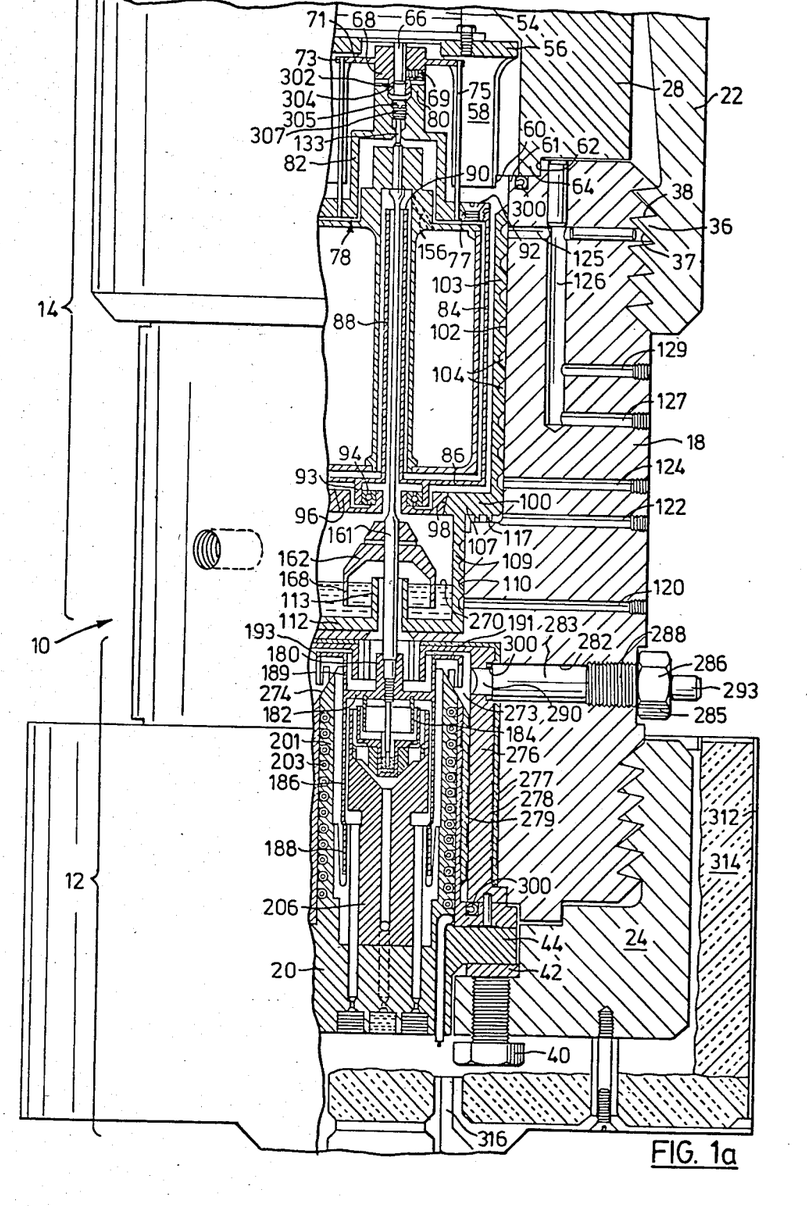
FIGS. 1a and 1b are bottom and top portions, respectively, of a partial axial sectional view.
Figure 1B:
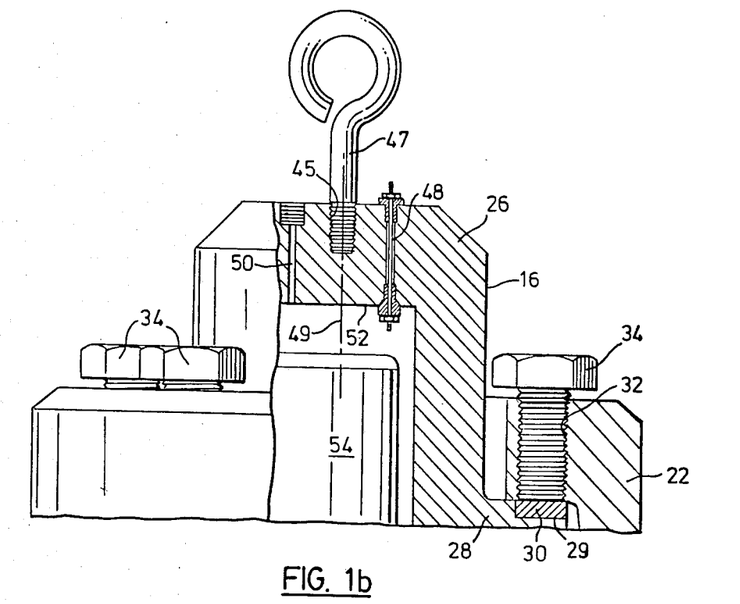

Attention is first directed to FIGS. 1a and 1b, in which a viscometer 10 includes a lower high temperature portion 12, and an upper low temperature portion 14.

Because the viscometer 10 is intended to contain very high pressures, up to 20,000 psi (1342 atmospheres), it incorporates an outer housing with very thick walls and strong construction, adapted to withstand such pressure. Looking at FIGS. 1a and 1b, the primary housing components include an upper cap 16, an intermediate sleeve 18, and a bottom plug 20. An upper nut 22 holds the upper cap 16 in position with respect to the sleeve 18, while a lower nut 24 holds the bottom plug 20 in position.

As can be seen, the upper cap 16 has a central hub 26 and an outer, lower flange 28. The flange 28 is recessed at 29 to receive an annular, hardened steel ring 30 (about 58 Rockwell C). The upper nut 22 has a plurality of threaded bores 32 adapted to receive a plurality of finely threaded bolts 34 which are positioned so as to bear downwardly against the hardened steel ring 30.

FIG. 1a shows that the threaded engagement of the upper nut 22 with the sleeve 18 is by way of engaging threads which are of buttress profile, such that the one flank of a tooth profile is less inclined than the other to the thread axis. In FIG. 1a, looking at the thread profile 36, the flank 37 is less inclined than the flank 38 to the thread axis, i.e. the general central vertical axis of the apparatus itself. It will be understood that the effect of placing a high internal pressure within the upper cap 16 will be to try to move the cap 16 upwardly with respect to the sleeve 18. This will place in compression the tooth profile flanks which are more inclined to the thread axis, i.e. the flank 38 and the mating flank of the sleeve 18. The engaging surfaces of these two flanks are more nearly perpendicular to the direction in which the internal pressure is attempting to separate the upper cap 16 and the sleeve 18.

It will be understood that the function of the upper nut 22 is to urge the upper cap 16 as tightly as possible against the sleeve 18, in order to effect a proper seal (the details of which will be explained subsequently). It is the function of the bolts 34 to accomplish the final phase of the tightening. Thus, the upper nut 22 is threaded onto the sleeve 18 as tightly as possible by hand, and then the individual bolts 34 are screwed downwardly through the upper nut 22, to bear downwardly against the steel ring 30 and the upper cap 16, thus forcing the latter against the sleeve 18.

The same construction applies at the bottom of the apparatus, between the lower nut 24 and the sleeve 18. Here, since the internal pressures are attempting to push the lower nut 24 downwardly with respect to the sleeve 18, the thread profiles are reversed. One of the tightening nuts is shown at 40, and this bears against a hardened steel ring 42, which in turn bears against a flange 44 of the bottom plug 20.

Looking now at FIG. 1b, the hub 26 of the upper cap 16 is centrally threaded at 45 to receive a hook 47 for the purpose of picking up and transporting the apparatus. The top of the hub 26 is machined to receive six electrical terminals 48, which are needed for the motor. The terminals incorporate at either end insulated conductors adapted to withstand very high pressures.

The hub 26 also has a nitrogen admission port 50 which allows pressurized nitrogen to be fed into a motor chamber 52 defined within the hub 26.

Located within motor chamber 52 is a stepping motor 54 of conventional construction, which has six input leads, connected separately to the different terminals 48.

It is known that stepping motors have the characteristic of being highly controllable in terms of rotational speed. The stepping motor operates on sequential electrical impulses, and each impulse moves the shaft of the stepping motor by 1.8°. Thus, it takes 200 impulses to cause the shaft of the motor to rotate through 360°.

The stepping motor 54 is mounted on a mounting plate 56 in the form of an annulus which has four integral downwardly extending pillars 58, each of which has a bottom portion which is stepped as shown at 60 so that it can be slip-fitted into engagement with a ledge 61 defined by the inner upper part of the sleeve 18. The latter has a recess 62 for receiving a boss 64 at the bottom inner region of the upper cap 16, for purposes of ease of assembly.

It will thus be seen that the mounting plate 56 rests by its own weight on the ledge 61, as it supports the stepping motor 54.

The shaft 66 of the stepping motor 54 has secured to it a boss 68 which is tightened into position by a set screw 69. The boss 68 has an annular flange 71 having four antipodal apertures 73 for receiving the ends of four upstanding spring wires 75. The wires 75 are typically made from high strength wire, and each is affixed in a portion 77 of a first turning member 78.

The construction of the first turning member 78 includes an upper boss 80, an outwardly and downwardly extending cup-shaped portion 82, the annular portion 77 described earlier, and an annular trough member 84 which extends first downwardly from the outer rim of the portion 77, with which it is threadedly engaged, thence inwardly to form a horizontal wall 86, thence upwardly to form a tube 88. The tube 88 terminates at an upper end 90, in a horizontal plane above the lower limit of the annular portion 77. The annular portion 77 has an oil filling plug 92.

The lower horizontal wall 86 of the first turning member 78 is integral with a downwardly projecting cylindrical flange 93, which encloses a ball bearing 94 supported by a tapered disc-like insert 96 sitting by gravity against a frusto-conical seat 98 defined by a stationary member 100 now to be described. As can be seen in FIG. 1a, the stationary member is shaped to fit snugly within a cylindrical centre cavity 102 within the sleeve 18. The stationary member 100 has an upstanding cylindrical portion 103 which is machined to define a spiral passage 104 between itself and the cavity 102 in the sleeve 18, and further includes an annular lower portion 107 which defines the frusto-conical seat 98 and has depending downwardly from it a cylindrical portion 109 adapted to fit snugly within a smaller-diameter cylindrical cavity 110. At the bottom of the cylindrical portion 109 is an integral, inwardly extending annular portion 112 which terminates in an upstanding tubular portion 113. The cylindrical portion 109, like the portion 103, is machined to provide a spiral passageway between itself and the cavity 110 of the sleeve 18.

The bottom surface of the annular portion 107 of the stationary member 100 has a spirally-running rib 117 which defines between its convolutions a spiralling passageway which is limited in part by a surface of the sleeve 18. The lower spiral passageway in the cylindrical portion 109 is connected to the inner end of the spiral passageway defined between the convolutions of the flange 117. A bore 120 is provided to deliver cooling water to the lower end of the spiral in the cylindrical portion 109, and a further bore 122 is provided to remove cooling water from the outer edge of the spiral passageway defined between the convolutions of the spiral flange 117. To provide a separate circuit, a bore 124 provides cooling water to the bottom end of the spiral passage 104, and a combination of bores 125, 126 and 127 provide an exit passageway for cooling water. A further bore 129 is provided to permit the entry of a temperature probe to check the exit temperature of the cooling water.

Figure 3:
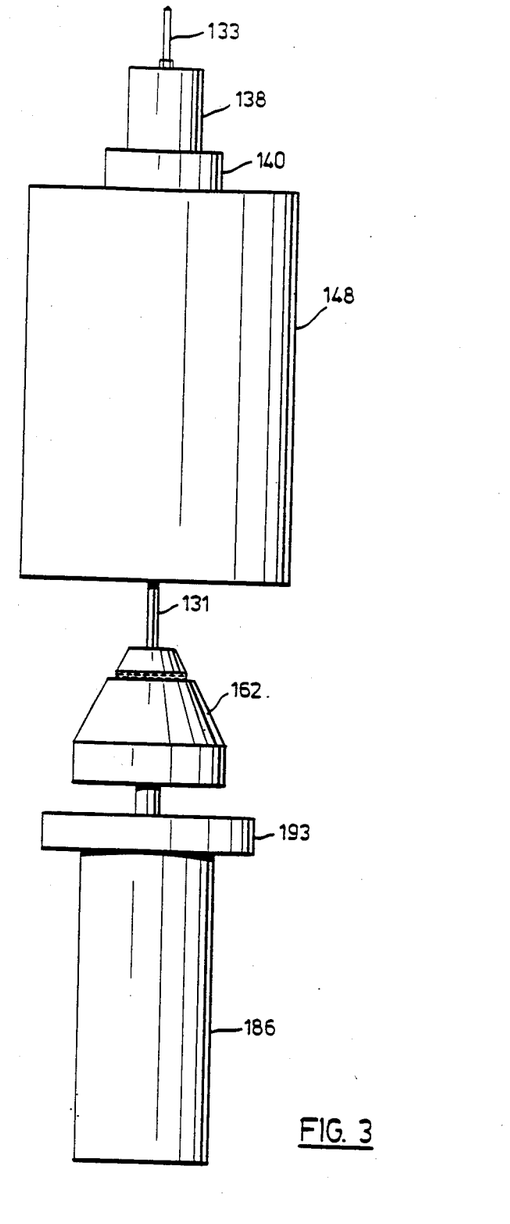
FIG. 3 is an elevation view of the rotary member forming part of the viscometer of FIGS. 1a and 1b.
Figure 4:
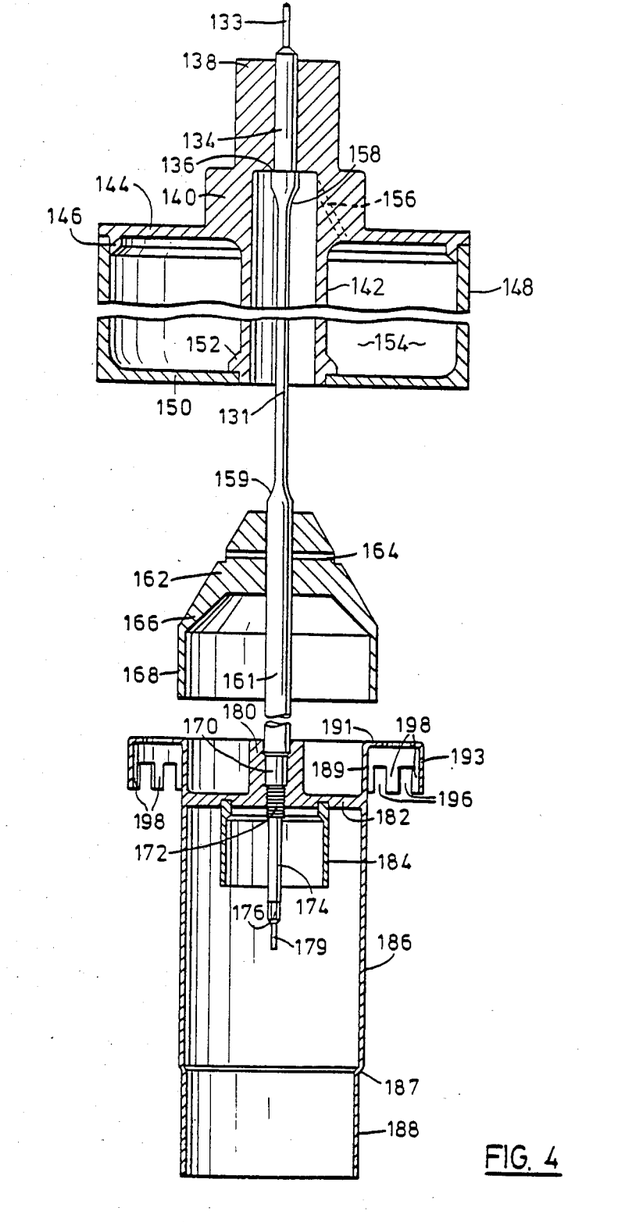
FIG. 4 is an axial sectional view through the rotary member shown in FIG. 3.

Attention is now directed to FIGS. 3 and 4, which illustrate the rotary member which is a primary component of the apparatus of this invention.

The various components of the rotary member are all secured to a central shaft shown at 131 in FIG. 4. At the top, the shaft 131 has a pin portion 133, which widens to a portion 134 which terminates in a slight outward step 136. The provision of the step 136 is to allow the seating of a boss 138. Depending downwardly from the boss 138 is an integral annular portion 140 from which downwardly extends a cylindrical tube 142 and from which outwardly extends an annular flange 144. The flange 144 has a downwardly extending cylindrical ridge 146 adapted to fit snugly within a cylindrical drum 148 that is integral at the bottom with an inwardly extending annular wall 150. The annular wall 150 registers with the tube 142 below a flange 152. The portions 138, 140, 142, 144, 158 and 150 are preferably all of plastic and the separate pieces are bonded together in any suitable way.

It will thus be seen that the tube 142, the drum 148, the flange 144 and the wall 150 enclose an annular volume 154. In order to allow for pressurization and depressurization of the basic apparatus, it is necessary to open the volume 154 through to the interior of the tube 142, and this is done by a drilled bore 156.

Below the step 136, the shaft 131 tapers to a smaller radius as shown at the numeral 158, and at this smaller dimension extends downwardly out of the tube 142. It then increases smoothly in diameter at 159 to transition to a larger diameter portion 161 on which a machine steel member 162 is mounted. The member 162 has an upper, solid, tapering portion provided with a tapped bore 164 through which a roll pin may be tightened to secure the member 162 in place on the shaft 131. The member 162 also defines an outwardly and downwardly flaring tapered portion 166 which terminates at the top of a downwardly depending cylindrical portion 168.

Below the member 162, the shaft 131 steps down to an intermediate diameter at 170, and then reduces again to define a threaded portion 172, below which it reduces again in diameter at 174, below which it defines a hex portion 176, finally terminating in a small-diameter pin portion 179.

Threadedly engaged with the threaded portion 172 of the shaft 131 is a hub 180, preferably of a metal such as titanium, which is integral at the bottom with an outwardly extending annular flange 182, the latter having an annular lower recess for receiving the upper end of a cylindrical member 184. At its outer extremity, the flange 182 is integral with a downwardly depending cylindrical portion 186, the latter having a slight inward step at 187 to provide a lower portion 188 of slightly smaller diameter. Above the flange 182 there is an upwardly extending cylindrical portion 189 which merges with an outwardly extending annular portion 191, the latter terminating in a downwardly extending cylindrical portion 193 in which is provided a plurality of gaps 196, thus defining a plurality of teeth 198.

Attention is now directed again to FIG. 2, for a description of the bottom plug 20 and its interaction with the lower portion of the rotary member shown in FIG. 4. The bottom plug 20 includes an upstanding cylindrical portion 201 in which is provided a helically wound, electrically insulated heating element 203. The heating element 203 is wrapped in a helical groove cut in the outside of the cylindrical portion 201. Thus, the heating element 203, when electrically energized, provides heat to the cylindrical portion 201.

Figure 2:
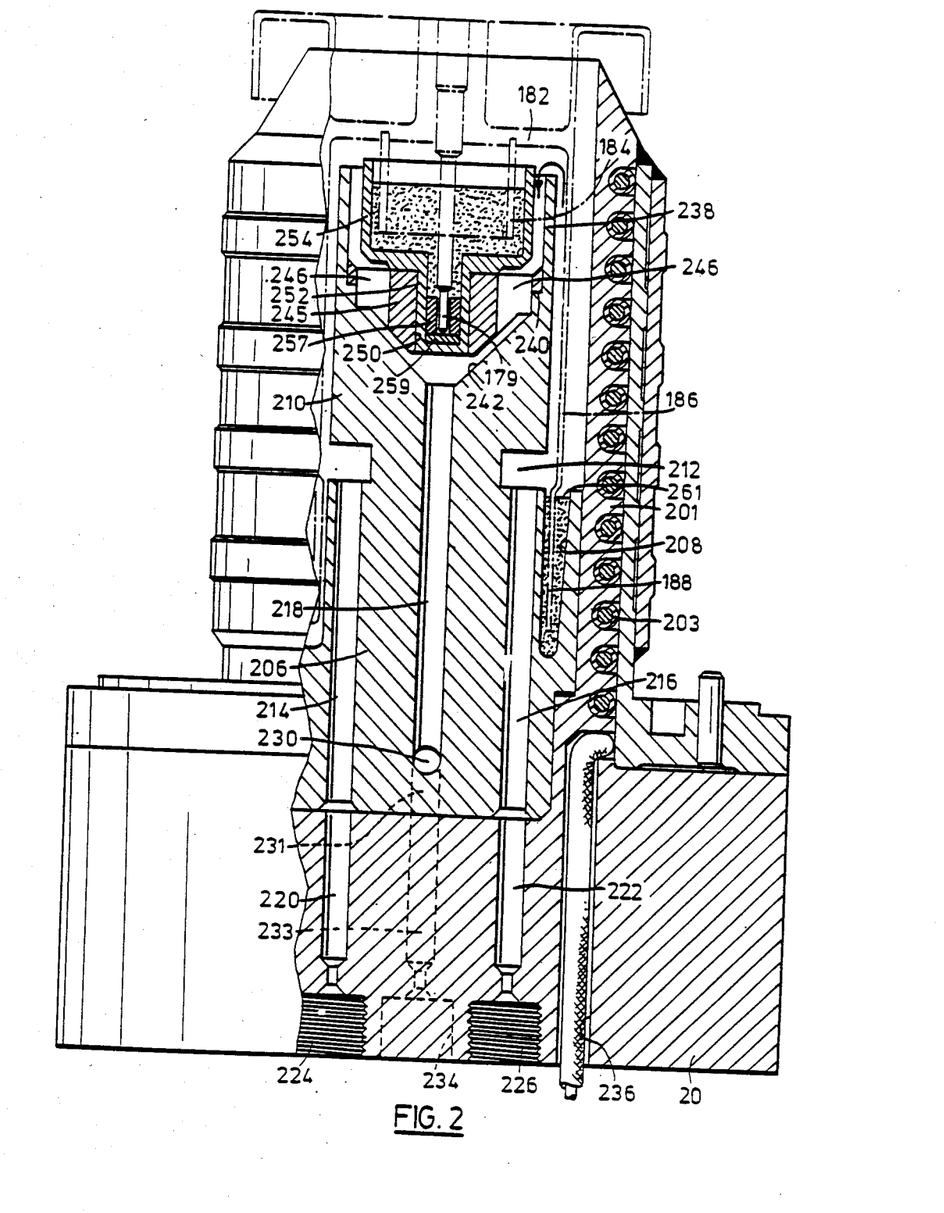

Seated within the cylindrical portion 201 is a central insert 206 which defines an upwardly open annular pocket 208 inwardly adjacent the cylindrical portion 201 and adapted to receive the lower portion 188 of the downwardly extending cylindrical portion 186 shown in FIG. 4. The insert 206 includes an upstanding boss 210 which is spaced inwardly from the internal wall of the cylindrical portion 201 of the bottom plug 20, thereby defining an annular passageway through which the cylindrical portion 186 freely extends, without contact. Likewise, the portion 188 is free of contact with the insert 206. At the bottom of the boss 210, there is provided an undercut which defines an annular gallery 212, the latter communicating with an entry passageway 214 through the insert 206, a temperature probe passageway 216 also through the insert 206, and an exit passageway 218 which extends centrally of the insert 206. The passageways 214 and 216 and 218 are located at an interval of 120° and it will be understood that FIG. 2 is therefore a section taken along two planes which converge at 120° at the central axis of the apparatus, the two planes passing through the passageways 214 and 216. The latter two passageways 214 and 216 communicate with corresponding passageways 220 and 222 in the bottom plug 20, and these latter communicate with corresponding threaded receptacles 224 and 226 which are adapted to receive high-pressure fittings. The central passageway 218 undergoes a lateral displacement along a lateral passage 230, and the latter communicates with the top of a short passageway 231 located at an angulation of 120° from both of the other passageways. The passageway 231 likewise communicates with a passageway 233 in the bottom plug 20, and the latter also has a threaded receptacle 234. A passageway 236 in the bottom plug 20 allows entry of the electrical heater element 203, and a similar passageway (not seen in the Figure) contains the other end of the element.

At the upper portion of the boss 210 there is defined an upstanding cylindrical portion 238 which begins at a step 240 atop a conical portion 242. The conical portion 242 communicates with the passageway 218.

Seated against this step 240 is a member 245 which is generally conical in outline, and contains a series of four vertical bore holes 246. It will be seen that the member 245 is out of contact with the conical portion 242 of the boss 210, and that the bore holes 246 allow communication between the passageway 218 and the region above the member 245. Centrally of the member 245 is a cylindrical recess 250 in which sits the hollow boss 252 of a cup-shaped member 254. The outer walls of the cup-shaped member 254 encompass but do not touch the cylindrical member 184 depending downwardly from the flange 182.

Centrally located within the hollow boss 252 is a bearing 257 which rests atop a disc 259. The bearing 257 surrounds the pin portion 179 of the shaft 131. The cup member 254 is partially filled with molten woods metal (molten at the operating temperatures), and thus woods metal surrounds the pin portion 179 and renders the latter self-centering. The self-centering tendency is contributed by all radially symmetrical surfaces of the rotary member which are in contact with liquid in shear.

The upwardly open annular pocket 208 is also filled with woods metal, to the level designated by the numeral 261, thus providing a seal between the inside and the outside of the cylindrical portion 186 of the rotary member. The word 'seal' is here used broadly to refer to the fact that the woods metal basically prevents contact between the test liquid and the nitrogen gas, whether or not a slight pressure differential may exist between them.

The drilling mud or other liquid to be tested passes upwardly along the passageway 214, into the gallery 212, upwardly along the inside surface of the cylindrical portion 186, then spills over to the inside of the cylindrical portion 238 extending upwardly from the boss 210, then passes through the holes 246 and finally returns downwardly along the passageway 218.

Looking at FIG. 1a, it will be seen that the annular channel defined by the cylindrical portion 109, the annular portion 112 and the tubular portion 113 of the stationary member 100 is filled with a liquid to the level marked 270. Preferably this liquid is silicone oil of low viscosity (typically 5 c.p.). The purpose of the oil, and of the member 162 of which the portion 168 extends downwardly into the oil, is to extract heat from shaft 161 at that location of the apparatus. It is intended that the hot portion be confined as closely as possible to the passageways along which the drilling mud moves, and this is the purpose of the cooling water passages, the oil in contact with the member 162, and the other spiral passage 104 for cooling water. When the shaft 131 and member 162 rotate, the oil shown at the level 270 is flung outwardly to expand its contact with the cylindrical portion 109.

It will be seen that the cylindrical portion 193 of the rotary member (that provided with the teeth 198) stands freely within a cavity 273 which is somewhat triangular in section. The triangularity is due to the frusto-conical surface 274 defined at the top of the cylindrical portion 201, along with the internal profile of an insert 276. The insert 276, and other cooperating inserts 277, 278 and 279, are intended to act as heat barriers, and their function is to help retain the heat generated by the heating element 203. Each of the inserts 276-279 has a plurality of shallow annular galleries in its outer surface, these providing regions where the inserts do not actually touch each other. This structure requires any heat transfer to be confined to a much smaller contact area.

Set into a suitable bore 282 in the sleeve 18 is a sound guide 283 which is made of a ceramic known by the trademark Macor. The sound guide 283 is fixed within a hollow bolt element 285 having a hexagonal portion 286 for rotation, and threads 288 for engagement with a threaded portion of the bore 282.

At its inner end, the sound guide 283 steps down to a smaller diameter portion 290 which has a concave spherical surface at its inner end, of which the centre of curvature lies on the surface of the cylindrical portion 193. Shown in FIG. 1a is a mount 293 for an ultrasound pulsing device, which may be of any known construction. The ultrasound pulsing device not only transmits sound into the sound guide, but detects an echo of the sound coming back from the spherical surface of the portion 290.

It will be appreciated that the spherical surface at the inside edge of the portion 290 of the sound guide 283 will pick up and transmit an echo of a sound pulse only when one of the teeth 198 is located at the centre of spherical curvature. Thus, as the teeth 198 pass in front of the portion 290, a series of ultrasonic echos will be returned to the ultra sound detector, and suitable circuitry is provided to determine the frequency of these echos, and thus the rotational speed of the rotary member.

A plurality of silver-plated inconel seals 300 are provided, in known fashion, to ensure retention of the very high pressures of operation.

The boss 80 has a central recess 302 which loosely surrounds a cylindrical projection 304 of the boss 68, thus centering the boss 80. The recess 302 communicates with a threaded bore 305 in which an adjustable set screw is threaded. The adjustable set screw determines the upper limit of movement of the shaft 131, by contact with the pin portion 133 of the shaft 131. Thus, the amount of vertical play for the shaft 131 can be determined by the setting of the set screw 307.

Pressurized nitrogen entering at the port 50 surrounds the stepping motor 54, communicates along the threaded bore 305 with the interior of the portion 82 below the boss 80, and enters the space between the annular trough member 84 and the inside wall of the portion 103. From there it can communicate through the ball bearing 94 to the inside of the tube 88, thence to the interior chamber 154 of the drum 148 along the bore 156. The nitrogen communicates further to the chamber containing the member 162, and can pass down through the non-sealed fit between the member 162 and the shaft 131. Thus, the nitrogen has access to the region around the hub 180, and thence to the chamber 273 and the annular space between the cylindrical portion 184 and the inside of the cylindrical portion 201. The pressurized nitrogen also has access along the shaft 131 within the hub 180 to the region above the woods metal within the cup member 254.

Surrounding the lower portion of the apparatus is a sheet-metal container 312 which contains insulation 314 spaced away from the internal portion of the apparatus. A fitting 316 is provided for air entry, when it is desired to quickly cool the lower portion of the apparatus after use. It is to be understood that various high pressure pipe fittings, etc. communicate with the threaded receptacles 224, 226 and 234.

In operation, a 50 c.p. silicone oil is admitted through the oil filling plug 92 to the level of the bottom of the annular flange 77, whereby the oil completely surrounds the member defined by the drum 148, the tube 142 and the wall 150. Drilling mud is pumped along the passageway 214 until it exits along the passageway 218, these two passageways being connected via high-pressured tubing to a circulation pump adapted to withstand the high pressures.

Nitrogen is then admitted to the apparatus through the port 50, to pressurize the apparatus to the desired level. Electrical energy is fed to the heating element 203 in order to heat the drilling mud, and circulation of the drilling is commenced.

Impulses are then fed to the stepping motor 54, which rotates the boss 68, the latter rotating the first turning member 78 by virtue of the wires 75. Due to viscous drag between the annular trough member 84 and the drum 148 (as well as the tube 142 and the wall 150), a torque is placed on the shaft 131, tending to rotate it, and also tending to rotate the cylindrical portion 186 suspended from the lower end of the shaft 131. The presence of the drilling mud adjacent the cylindrical portion 186, however, places a retarding drag on the shaft 131. When equilibrium is reached, the torque transmitted to the upper portion of the shaft 131 is the same as the retarding torque exerted by the drilling mud at the bottom.

Prior calibration of the effect of the oil within the annular trough member 84 allows an accurate determination of the torque applied to the shaft 131 at the top, simply by noting the difference in the rotational rates of the stepping motor 54 and the shaft 131. The combination of this factor, the actual rotational speed of the shaft 131, and the geometry of the annular volume containing the drilling mud, allows the viscosity of the drilling mud under the extreme temperature and pressure conditions to be calculated.

It will be appreciated that the use of the oil within the annular trough member 84 permits the viscosity range of the apparatus to be changed without requiring a change of hardware. More specifically, by changing the temperature of the oil within the annular trough member 84, a fine adjustment of the viscosity of the oil can be effected, thus permitting a fine tuning or fine adjustment of the viscosity range which the apparatus will measure. Alternatively, by replacing the oil with an oil of different viscosity, a gross adjustment of the viscosity range can be carried out.

The rotary member shown in FIG. 3 effectively floats in the two chambers carrying woods metal and in the oil within the annular trough member 84. The pressurization of the apparatus affects the floating level, since it governs the weight of (mainly) nitrogen within the volume 154. At an intermediate pressure the rotary member can be suspended without axial pressure at the ends of the shaft 131, thereby eliminating the effects of bearing friction.

It will be appreciated that the method and apparatus disclosed herein could be utilized for the testing of fluid media other than drilling mud, for example oils, greases, foodstuffs and plastics.

There has thus been provided an apparatus capable of measuring shear rate and shear stress of a test liquid over a substantial range of temperature and pressure. Additionally, the apparatus disclosed herein is capable of measuring the gel strength of non-Newtonian or thixotropic liquids. There are two methods by which this may be carried out.

In the first method, the stepping motor is accelerated at the maximum gradient, and the difference between the rotational speed of the shaft 131 and the stepping motor is measured when the latter reaches an rpm which equates to a shear rate of 5.11 sec.$^{-1}$, which is the industry standard.

The second method is to gradually increase the stepping motor rotational speed, and then measure the difference between the rotational speed of the shaft 131 and that of the stepping motor when the first signal comes from the ultrasonic measurement device (indicating that the shaft 131 has begun to rotate).

The apparatus of the present invention has a flow-through capability with respect to the test liquid, due to the presence of an outside pump to circulate the test liquid (the pump is not shown in the drawings).

It will be appreciated that one advantage of the apparatus of this invention is the possibility to operate and monitor it from a remote, safe station. This is important due to the fact that very high pressures are being utilized.

While one embodiment of this invention has been illustrated in the accompanying drawings and described hereinabove, it will be apparent to those skilled in the art that changes and modifications may be made therein without departing from the essence of this invention, as set forth in the appended claims.

I claim:

1. An apparatus for measuring the viscosity of a fluid medium, comprising:
   means for rotating a first member at an accurately known rate,
   a freely turning rotary member having an axis of rotation and having a first portion adjacent said first member but out of contact therewith,
   a first fluid cavity between said first member and said first portion,
   a fluid being located in said first fluid cavity such that rotation of the first member will place torque on said rotary member thus seeking to induce rotation therein,
   the rotary member having a second portion moving adjacent a fixed surface but out of contact therewith,
   a second fluid cavity between said second portion and the fixed surface into which can be placed said fluid medium of which the viscosity is to be measured,
   and means to measure the rotational speed of the rotary member.

2. The apparatus claimed in claim 1, in which the means for rotating the first member is an electrical motor, and in which the motor, the first member, and the entire rotary member are located within a chamber adapted to be sealed from the ambience and to contain superatmospheric pressure.

3. The apparatus claimed in claim 2, in which the second portion of the rotary member is thermally isolated from the first portion and the motor, the apparatus further comprising means for heating the fluid medium.

4. The apparatus claimed in claim 3, in which the means for heating includes electrical resistance elements adjacent said fixed surface.

5. The apparatus claimed in claim 3, which further includes means for circulating the fluid medium through said second fluid cavity.

6. The apparatus claimed in claim 2, in which the electrical motor is a stepping motor, and in which the fluid in the first fluid cavity is a Newtonian oil having controllable rheological properties whereby any given rotational speed differential between the first member and the first portion of the rotary member can be taken to indicate a particular value of torque applied to the rotary member.

7. The apparatus claimed in claim 6, in which the axis of rotation is vertical, in which said first member includes an internal cylindrical surface concentric with said axis of rotation of the rotary member, and in which said first portion of the rotary member includes an external cylindrical surface concentric with said axis of rotation and within said internal cylindrical surface.

8. The apparatus claimed in claim 7, in which said fixed surface is a fixed external cylindrical surface concentric with said axis of rotation, and in which said second portion of the rotary member includes an internal cylindrical surface concentric with said axis of rotation and surrounding said fixed external cylindrical surface.

9. The apparatus claimed in claim 8, in which the internal cylindrical surface of the second portion is the inner surface of a hollow cylinder with an open bottom end, said bottom end being received into a cylindrical pocket of which part defines said fixed external cylindrical surface, the cylindrical pocket containing molten woods metal into which the said bottom end is immersed, thereby providing a seal between the said second fluid cavity on the inside of the hollow cylinder, and a third fluid cavity external to the hollow cylinder.

10. The apparatus claimed in claim 9, in which said first portion of the rotary member is the outer surface of a hollow cylindrical drum which is concentric with said axis of rotation, said first member defining an internal cylindrical surface surrounding said drum, and in which said third fluid cavity is in communication with the interior of said drum, the apparatus including means for admitting nitrogen under pressure into said chamber.

11. The apparatus claimed in claim 7, in which the rotor is self-centering due to the oil in the first fluid cavity.

12. The apparatus claimed in claim 10, in which the rotor is self-centering due to the oil in the first fluid cavity and the fluid medium in the second fluid cavity.

13. The apparatus claimed in claim 2, in which the rotary member has affixed thereto a flange member having regularly spaced gaps equidistant from said axis of rotation, the flange member being within said chamber, said means to measure the rotation speed including means for directing a signal toward said flange and for receiving a returning echo therefrom when the signal falls on the flange between the gaps, whereby the frequency of the echo receptions has a known direct proportionality to the rotational speed of the rotary member.

14. The apparatus claimed in claim 13, in which the flange is a toothed cylinder, and the signal is an ultrasonic signal.

15. The apparatus claimed in claim 14, in which the ultrasonic signal is directed radially inwardly toward the toothed cylinder, and in which there is provided, inwardly of the cylinder, a conical sound deflector adapted to deflect obliquely away from the echo receiving means an ultrasonic signal passing through the gap between the teeth.

16. The apparatus claimed in claim 2, in which the chamber is defined between at least two housing members, the housing members having engaging threads which are of sawtooth profile such that one flank of a tooth profile is less inclined than the other to the thread axis, the internal pressure within the chamber placing in compression the tooth profile flanks which are more inclined to the thread axis.

17. The apparatus claimed in claim 16, in which threaded bolt means are threadably engaged in one of the housing members and upon tightening bears against another of the housing members in a direction aligned with said thread axis, thereby locking the threads together.

18. A method of measuring the viscosity of a fluid medium, comprising the steps of:
using viscous drag means for applying a torque-induced rotation to a rotary member, in such a way that the torque on the rotary member can be known,
placing the fluid medium in a fluid cavity defined between a portion of the rotary member and a fixed surface,
determining the torque applied to the rotary member through the viscous drag thereon from a prior calibration,
and determining the viscosity of the fluid medium from the geometry of the fluid cavity, the known torque on the rotary member, and the rotational speed of the rotary member.

19. A method of determining the viscosity of a fluid medium, comprising the steps:
rotating a first member at a given rate,
using viscous drag to cause the rotating first member to rotate a rotary member about an axis of rotation thereof,
providing a fluid cavity between a portion of the rotary member and a fixed surface and placing the fluid medium therein, and
measuring the rotational speed of the rotary member,
whereby the geometry of the fluid cavity, the rotational speed of the rotary member, and a precalibrated relation between torque on the rotary member and the slip between the latter and the first member allow a calculation of the viscosity of the fluid medium.

20. The method claimed in claim 19, in which the first member is rotated by an electrical stepping motor, and in which the motor, the first member, and the entire rotary member are under superatmospheric pressure.

21. The method claimed in claim 20, in which the fluid medium is heated in said fluid cavity.

22. The method claimed in claim 21, in which the fluid medium is drilling mud, and is circulated through said fluid cavity.

23. The method claimed in claim 20, in which a flange on the rotary member provided with regularly spaced gaps rotates past a device for directing a signal toward the flange, and for receiving a returning echo therefrom when the signal falls on the flange between the gaps, the method including determining the rotational speed of the rotary member on the basis of the frequency of the echo receptions.

24. The method claimed in claim 23, in which the signal is an ultrasonic signal.

25. The apparatus claimed in claim 2, in which the rotary member is buoyantly supported by the fluid in said first fluid cavity, whereby the rotary member may be out of mechanical contact with surrounding parts of the apparatus.

26. The method claimed in claim 19, in which the step of using viscous drag is performed by placing a liquid between adjacent coaxial surfaces of revolution on said first member and said rotary member, and in which the viscosity of said fluid is selected to obtain a desired accuracy range and a desired range of viscosity determination for the fluid medium to be tested.

27. The apparatus claimed in claim 1, in which the fluid in said first fluid cavity is a silicone oil.

28. The appartus claimed in claim 27, in which the viscosity of the silicone oil is about 50 c.p.

29. A method of measuring the gel strength of a thixotropic liquid, comprising the steps of:
providing a first member adapted to be rotated at a variable, known rate,
providing viscous drag means to cause the rotating first member to attempt to rotate a rotary member about an axis of rotation thereof,
providing a fluid cavity between a portion of the rotary member and a fixed surface and placing the thixotropic liquid therein,
accelerating the first member at maximum gradient,
when the rotating first member reaches a rotational speed which equates to a shear rate of 5.11 sec.$^{-1}$, measuring the differential speed between the first member and the rotary member,
and using the geometry of the fluid cavity, the rotational speed of the rotary member, and a precalibrated relation between torque on the rotary member and the slip between the latter and the first member to calculate the gel strength of the thixotropic liquid.

30. A method of determining the gel strength of a thixotropic liquid, comprising the steps:
providing a first member which can be rotated at a known, variable rate,
providing viscous drag means to permit the rotating first member to rotate a rotary member about an axis of rotation thereof,
providing a fluid cavity between a portion of the rotary member and a fixed surface and placing the thixotropic liquid therein,
gradually increasing the rotational speed of the first member from 0, and measuring the rotational speed of the rotating first member when the rotary member begins to rotate.

31. The method claimed in claim 30, in which a flange on the rotary member provided with regularly spaced gaps rotates past a device for directing a signal towards the flange, and for receiving the echo therefrom when the signal falls on the flange between the gaps.

* * * * *

UNITED STATES PATENT AND TRADEMARK OFFICE
CERTIFICATE OF CORRECTION

PATENT NO. : 4,630,468

DATED : December 23, 1986

INVENTOR(S) : Edmund G. F. Sweet

It is certified that error appears in the above-identified patent and that said Letters Patent is hereby corrected as shown below:

On the title page, Item [73] should read

-- [73] Assignee: Trans-Canada Resources Ltd., Alberta, Canada --.

Signed and Sealed this

Twenty-seventh Day of October, 1987

Attest:

DONALD J. QUIGG

*Attesting Officer*   *Commissioner of Patents and Trademarks*